(12) United States Patent
Zheng

(10) Patent No.: US 10,772,604 B2
(45) Date of Patent: Sep. 15, 2020

(54) FOLDABLE ULTRASONIC SENSING DEVICE

(71) Applicants: Interface Technology (ChengDu) Co., Ltd., Chengdu (CN); INTERFACE OPTOELECTRONICS (SHENZHEN) CO., LTD., Shenzhen (CN)

(72) Inventor: Xiao-Bing Zheng, Shenzhen (CN)

(73) Assignees: Interface Technology (ChengDu) Co., Ltd., Chengdu (CN); INTERFACE OPTOELECTRONICS (SHENZHEN) CO., LTD., Shenzhen (CN)

( * ) Notice: Subject to any disclaimer, the term of this patent is extended or adjusted under 35 U.S.C. 154(b) by 810 days.

(21) Appl. No.: 15/475,607

(22) Filed: Mar. 31, 2017

(65) Prior Publication Data

US 2018/0199917 A1    Jul. 19, 2018

(30) Foreign Application Priority Data

Jan. 16, 2017  (CN) .......................... 2017 1 0032365

(51) Int. Cl.
*A61B 8/00*    (2006.01)
*G01S 7/52*    (2006.01)
*G01S 15/89*    (2006.01)

(52) U.S. Cl.
CPC .......... *A61B 8/4444* (2013.01); *A61B 8/4466* (2013.01); *A61B 8/4483* (2013.01); *G01S 7/52079* (2013.01); *G01S 15/8934* (2013.01)

(58) Field of Classification Search
CPC ... A61B 8/4444; A61B 8/4483; A61B 8/4466; G01S 15/8934; G01S 7/52079
See application file for complete search history.

(56) References Cited

U.S. PATENT DOCUMENTS

2015/0313572 A1*  11/2015  Gerbaulet ............ A61B 8/0875
                                                                            433/29
2016/0338663 A1*  11/2016  Chen .................... A61B 8/4254

* cited by examiner

*Primary Examiner* — Amelie R Davis
(74) *Attorney, Agent, or Firm* — ScienBiziP, P.C.

(57) ABSTRACT

An ultrasonic sensing device is foldable and includes two bracket portions rotatably connected and an ultrasonic sensor on each bracket portion. The ultrasonic sensor includes a flexible circuit board carrying an ultrasonic signal transmitting element and an ultrasonic signal receiving element. The ultrasonic signal transmitting element is mounted to one of the two bracket portions, and the ultrasonic signal receiving element is mounted to other of the two bracket portions. The ultrasonic signal transmitting element is capable of rotating to the ultrasonic signal receiving element by opening and closing the two bracket portions.

14 Claims, 6 Drawing Sheets

FOLDABLE ULTRASONIC SENSING DEVICE

FIELD

The subject matter herein generally relates to a foldable ultrasonic sensing device.

BACKGROUND

Ultrasonic sensors have many advantages such as small size, low cost, safe, and widespread use as medical devices. The ultrasonic sensors can be used for medical diagnosis. However, results obtained from current unwieldy ultrasonic sensors may not be accurate. Therefore, there is room for improvement in the art.

BRIEF DESCRIPTION OF THE DRAWINGS

Implementations of the present technology will now be described, by way of example only, with reference to the attached figures.

DETAILED DESCRIPTION

Figure 1:
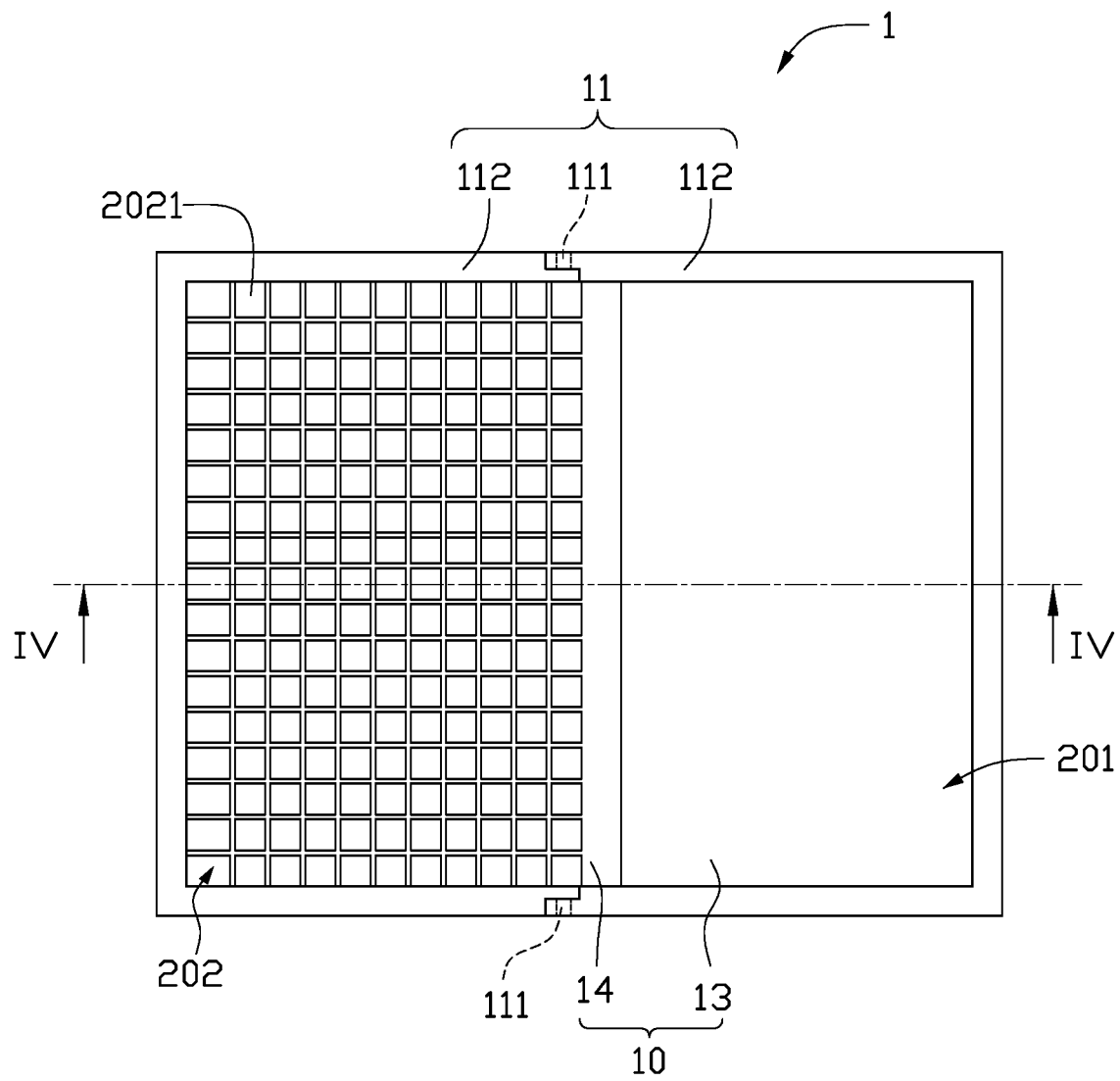
FIG. 1 is planar view of an exemplary embodiment of an ultrasonic sensing device.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein may be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts may be exaggerated to better illustrate details and features of the present disclosure.

The term "coupled" is defined as connected, whether directly or indirectly through intervening components, and is not necessarily limited to physical connections. The connection can be such that the objects are permanently connected or releasably connected. The term "comprising" when utilized, means "including, but not necessarily limited to"; it specifically indicates open-ended inclusion or membership in the so-described combination, group, series, and the like.

Figure 2:
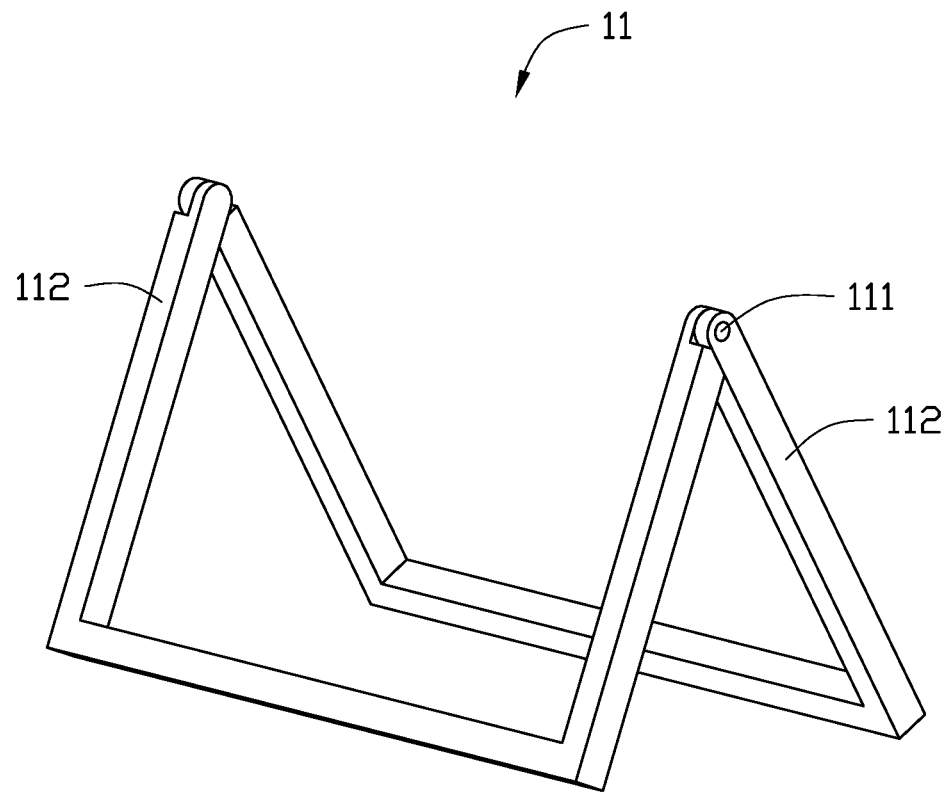
FIG. 2 is an isometric view of a first exemplary embodiment of a bracket of the ultrasonic sensing device of FIG. 1.

FIG. 1 illustrates an ultrasonic sensing device 1 according to an exemplary embodiment. The ultrasonic sensing device 1 includes a bracket 11 and an ultrasonic sensor 10 mounted on the bracket 11. As shown in FIG. 2 where the sensors 10 are not assembled, the bracket 11 is foldable like a book and includes two bracket portions 112 rotably connected to each other. An angle formed between the two bracket portions 112 is adjustable between 0 and 180 degrees. FIG. 1 shows the angle formed by the two bracket portions 112 is close to 180 degrees. In the exemplary embodiment, the two bracket portions 112 are rotably connected to each other by two hinges 111, enabling the two bracket portions 112 to be folded together or unfolded. Each hinge 11 is located between the two bracket portions 112.

As shown in FIG. 1 and FIG. 2, each bracket portion 112 is substantially a "U" shape; and the two bracket portions 112 cooperatively form a closed and substantially rectangular ring when the two bracket portions 112 are completely unfolded. As shown in FIG. 1, the ultrasonic sensor 10 is surrounded by the two bracket portions 112.

In the exemplary embodiment, the ultrasonic sensor 10 and the bracket portions 112 are coupled together by a binder (not shown), and the binder is positioned between the ultrasonic sensor 10 and the bracket portions 112.

Figure 3:
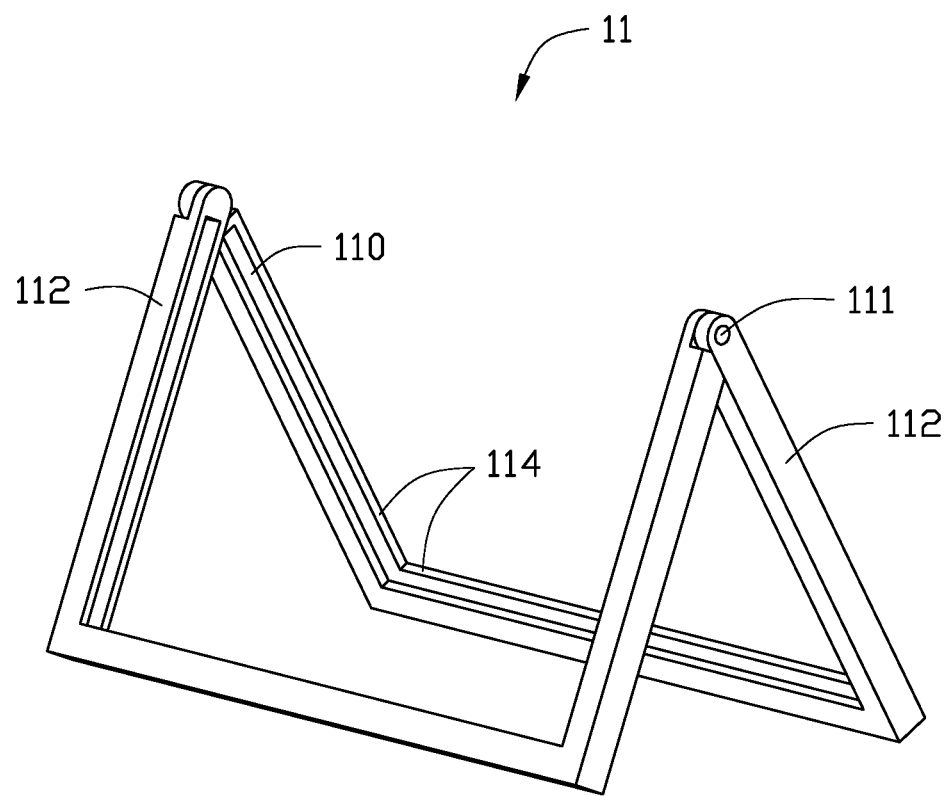
FIG. 3 is an isometric view of a second exemplary embodiment of the bracket of the ultrasonic sensing device of FIG. 1.

As shown in FIG. 3 where the sensors 10 are not assembled, another exemplary embodiment, each bracket portion 112 includes an inner surface 114 facing the ultrasonic sensor 10. At least one receiving groove 110 is defined in the inner surface 114, and a peripheral portion of the ultrasonic sensor 10 is received in the receiving groove 110.

Figure 4:
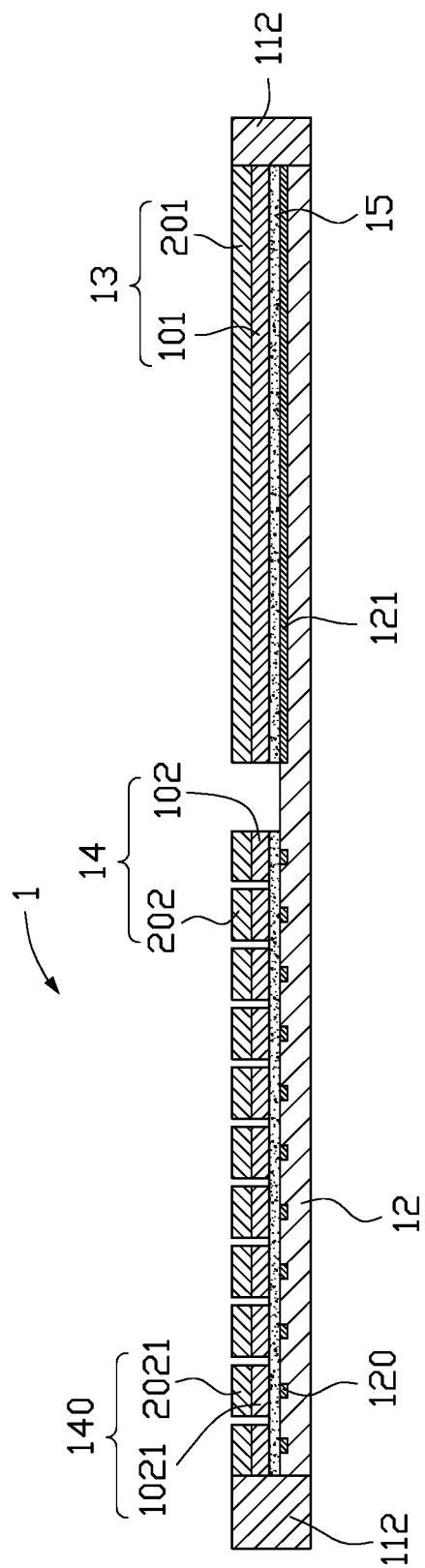
FIG. 4 is a cross-sectional view of the ultrasonic sensing device along line IV-IV of FIG. 1.

FIG. 4 illustrates the ultrasonic sensor 10 according to an exemplary embodiment. The ultrasonic sensor 10 includes a flexible circuit board 12, an ultrasonic signal transmitting element 13, and an ultrasonic signal receiving element 14 formed on the flexible circuit board 12. The flexible circuit board 12 is mounted to the two bracket portions 112. The flexible circuit board 12 can be folded or unfolded with the bracket portions 112.

Figure 5:
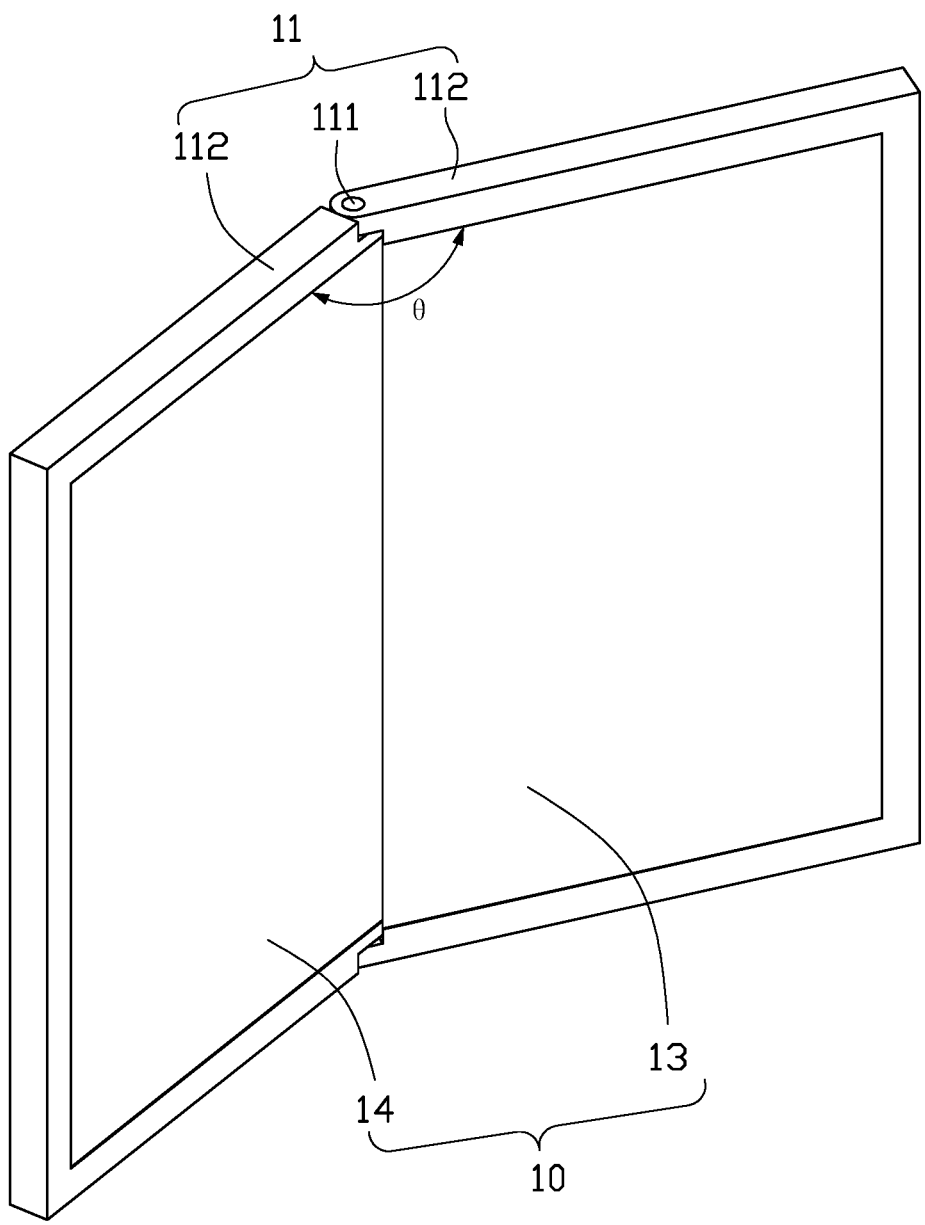
FIG. 5 is an isometric view of the ultrasonic sensing device of FIG. 1.

As shown in FIG. 4, the ultrasonic signal transmitting element 13 and the ultrasonic signal receiving element 14 are formed at a same side of the flexible circuit board 12. The ultrasonic signal transmitting element 13 and the ultrasonic signal receiving element 14 do not overlap with each other. The ultrasonic signal transmitting element 13 and the ultrasonic signal receiving element 14 are positioned at different regions of the flexible circuit board 12. The ultrasonic signal transmitting element 13 is surrounded by one bracket portion 112, and the ultrasonic signal receiving element 14 is surrounded by the other bracket portion 112. Thereby, the ultrasonic signal transmitting element 13 can be rotated towards the ultrasonic signal receiving element 14 by rotating one bracket portion 112 to other bracket portion 112. FIG. 5 illustrates that the ultrasonic signal transmitting element 13 and the ultrasonic signal receiving element 14 between form an angle of θ, which is less than 180 degrees.

The flexible circuit board 12 can be a flexible printed circuit board or a flexible thin-film transistor board. As shown in FIG. 4, the flexible circuit board 12 includes a reference electrode 121 corresponding to the ultrasonic signal transmitting element 13 and a plurality of sensing electrodes 120 corresponding to the ultrasonic signal receiving element 14.

As shown in FIG. 4, the ultrasonic signal transmitting element 13 includes the reference electrode 121, a first piezoelectric material layer 101 stacked on the reference electrode 121, and a first electrode layer 201 stacked on the first piezoelectric material layer 101. The first piezoelectric material layer 101 is positioned between the reference electrode 121 and the first electrode layer 201. The reference electrode 121 and the first electrode layer 201 cooperatively form an electrical field, and the first piezoelectric material layer 101 vibrates and produces ultrasonic wave under the electrical field. In this exemplary embodiment, the reference electrode 121 can be grounded.

As shown in FIG. 4, the ultrasonic signal receiving element 14 includes the plurality of sensing electrodes 120, a second piezoelectric material layer 102 stacked on the plurality of sensing electrodes 120, and a second electrode layer 202 stacked on the second piezoelectric material layer 102. The second piezoelectric material layer 102 is discontinuous and includes a plurality of piezoelectric material units 1021 spaced apart from each other. The second electrode layer 202 is discontinuous and includes a plurality of electrode units 2021 spaced apart from each other. Each of the plurality of piezoelectric material units 1021, one corresponding sensing electrode 120, and one corresponding electrode unit 2021 cooperatively form an ultrasonic signal receiving unit 140. Thus, ultrasonic signal receiving element 14 includes a plurality of ultrasonic signal receiving units 140. Each ultrasonic signal receiving unit 140 is capable of receiving ultrasonic signals independently and producing sensing charges independently.

In the exemplary embodiment, a controlling circuit (not shown) is set on the flexible circuit board 12 and the controlling circuit includes the plurality of sensing electrodes 120. That is, the plurality of sensing electrodes 120 is a portion of the controlling circuit. The plurality of sensing electrodes 120 is configured to collect the sensing charges and input the sensing charges to the controlling circuit.

In the exemplary embodiment, both the first piezoelectric material layer 101 and the second piezoelectric material layer 102 are adhered to the flexible circuit board 12 by a binder layer 15. That is, a binder layer 15 is positioned between the reference electrode 121 and the first piezoelectric material layer 101 and another binder layer 15 is positioned between the plurality of sensing electrodes 120 and the second piezoelectric material layer 102. The binder layer 15 has a square resistance of less than 150 Ω/sq cm, a dielectric constant of less than 5 F/m.

Both the first piezoelectric material layer 101 and the second piezoelectric material layer 102 are made of a piezoelectric material, such as polyvinylidene fluoride and lead zirconate titanate piezoelectric ceramic. In one exemplary embodiment, the first piezoelectric material layer 101 is made of lead zirconate titanate piezoelectric ceramic. Lead zirconate titanate piezoelectric ceramic is capable of producing ultrasonic waves having high intensities. The second piezoelectric material layer 102 is made of polyvinylidene fluoride, as polyvinylidene fluoride has a good ability of absorbing ultrasonic waves and can obtain ultrasonic wave signals having high intensities.

The first electrode layer 201 and the second electrode layer 202 are made of an electrically-conductive material, such as silver, cooper, molybdenum, or indium tin oxide. The first electrode layer 201 and the second electrode layer 202 can be the same electrically-conductive material and formed at a same time.

In use, the ultrasonic signal transmitting element 13 of the ultrasonic sensing device 1 is held against skin of a human body at a position corresponding to a target area to be investigated. For example, the object to be investigated is a heart of a human being. Voltage is applied to first electrode layer 201, an electric field (not shown) is formed between the first electrode layer 201 and the reference electrode 121, and the first piezoelectric material layer 101 vibrates and produces ultrasonic waves under the electric field. The ultrasonic waves pass through the skin and subcutaneous fatty tissue and reach the heart. The heart reflects the ultrasonic waves back to the ultrasonic signal receiving element 14, and the ultrasonic signal receiving element 14 receives the reflected ultrasonic signals and converts the reflected ultrasonic signals to electrical signals. The reflected ultrasonic waves are received by the second piezoelectric material layer 102, and the second piezoelectric material layer 102 produces sensing charges. The sensing charges are collected by the plurality of sensing electrodes 120 and input to the controlling circuit.

Figure 6:
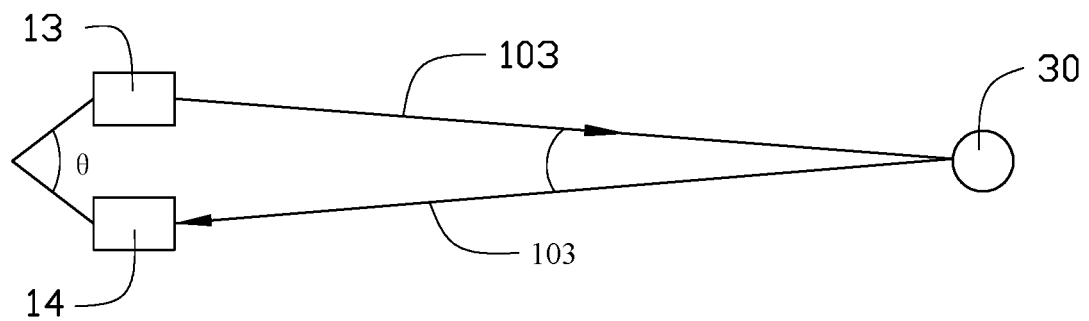
FIG. 6 is a schematic diagram demonstrating the working principle of the ultrasonic sensing device of FIG. 1.

As shown in FIG. 6, the ultrasonic signal transmitting element 13 and the ultrasonic signal receiving element 14 form an angle θ that is less than 180 degrees. The ultrasonic signal transmitting element 13 sends ultrasonic waves 103 to an object 30, and the object 30 reflects the ultrasonic waves 103 back to the ultrasonic signal receiving element 14. The intensity of the waves 103 received by the ultrasonic signal receiving element 14 can be adjusted by adjusting the angle θ.

In other exemplary embodiments, each bracket portion 112 may have a shape other than a "U" shape. For example, each bracket portion 112 can have a C shape, or each bracket can have a planar board shape. When each bracket portion 112 has a planar board shape, the ultrasonic signal transmitting element 13 and the ultrasonic signal receiving element 14 may be located at a same side of the two bracket portions 112. Herein, the ultrasonic signal transmitting element 13 is stacked on one of the two bracket portions 112, and the ultrasonic signal receiving element 14 is stacked on the other one of the two bracket portions 112. In other exemplary embodiments, the two bracket portions 112 may be rotably connected to each other by other connecting elements and not limited by hinges 111.

In other exemplary embodiments, the ultrasonic sensing device 1 includes two protecting layers (not shown). Each of the two protecting layers covers one of the opposite sides of the flexible circuit board 12. One of the two protecting layer covers the ultrasonic signal transmitting element 13 and the ultrasonic signal receiving element 14, and the other one of the two protecting layer covers a surface of the flexible circuit board 12 away from the ultrasonic signal transmitting element 13 and the ultrasonic signal receiving element 14. The two protecting layers are flexible and can be folded and unfolded together with the flexible circuit board 12.

It is to be understood, even though information and advantages of the present exemplary embodiments have been set forth in the foregoing description, together with details of the structures and functions of the present exemplary embodiments, the disclosure is illustrative only. Changes may be made in detail, especially in matters of shape, size, and arrangement of parts within the principles of the present exemplary embodiments to the full extent indicated by the plain meaning of the terms in which the appended claims are expressed.

What is claimed is:

1. A foldable ultrasonic sensing device comprising:
    two bracket portions moveably connected to each other;
    an ultrasonic sensor mounted to the two bracket portions;
    wherein the ultrasonic sensor comprises a flexible circuit board, an ultrasonic signal transmitting element configured to produce ultrasonic waves, and an ultrasonic signal receiving element configured to receive ultrasonic waves; wherein the ultrasonic signal transmitting element and the ultrasonic signal receiving element are formed on a same side of the flexible circuit board;
    wherein the ultrasonic signal transmitting element is mounted to one of the two bracket portions, and the ultrasonic signal receiving element is mounted to the other one of the two bracket portions; the ultrasonic signal transmitting element is capable of moving relative to the ultrasonic signal receiving element by moving one of the two bracket portions to the other bracket portion.

2. The foldable ultrasonic sensing device of claim 1, wherein the flexible circuit board is mounted to the two bracket portions; and the flexible circuit board is configured to be folded or unfolded by moving one of the two bracket portions relative to the other bracket portion.

3. The foldable ultrasonic sensing device of claim 1, wherein the ultrasonic signal transmitting element comprises a reference electrode on the flexible circuit board, a first piezoelectric material layer stacked on the reference electrode, and a first electrode layer stacked on the first piezoelectric material layer.

4. The foldable ultrasonic sensing device of claim 3, wherein the first piezoelectric material layer is made of a lead zirconate titanate piezoelectric ceramic.

5. The foldable ultrasonic sensing device of claim 3, wherein the reference electrode is electrically grounded.

6. The foldable ultrasonic sensing device of claim 1, wherein the ultrasonic signal receiving element comprises at least one sensing electrode on the flexible circuit board, a piezoelectric material layer stacked on the at least one sensing electrode, and an electrode layer stacked on the piezoelectric material layer.

7. The foldable ultrasonic sensing device of claim 6, wherein the at least one sensing electrode comprises a plurality of sensing electrodes, the second piezoelectric material layer comprises a plurality of piezoelectric material units spaced apart from each other; the second electrode layer comprises a plurality of electrode units spaced apart from each other; the ultrasonic signal receiving element comprises a plurality of ultrasonic signal receiving units, wherein each of the plurality of ultrasonic signal receiving units comprises one of the piezoelectric material units, one of the sensing electrodes, and one of the electrode units.

8. The foldable ultrasonic sensing device of claim 7, wherein each ultrasonic signal receiving unit is capable of receiving ultrasonic signals independently.

9. The foldable ultrasonic sensing device of claim 6, wherein the second piezoelectric material layer is made of polyvinylidene fluoride.

10. The foldable ultrasonic sensing device of claim 1, wherein the flexible circuit board is a flexible printed circuit board or a flexible thin-film transistor board.

11. The foldable ultrasonic sensing device of claim 1, wherein the two bracket portions are moveably connected to each other by at least one hinge.

12. The foldable ultrasonic sensing device of claim 1, wherein the two bracket portions cooperatively form a ring, the ultrasonic sensor is surrounded by the two bracket portions.

13. The foldable ultrasonic sensing device of claim 12, wherein each bracket portion has substantially a U shape.

14. The foldable ultrasonic sensing device of claim 12, wherein each bracket portion includes an inner surface facing the ultrasonic sensor, at least one receiving groove is defined in the inner surface; a peripheral portion of the ultrasonic sensor is received in the at least one receiving groove.

\* \* \* \* \*